(12) United States Patent
Kamei et al.

(10) Patent No.: US 7,790,470 B2
(45) Date of Patent: Sep. 7, 2010

(54) STIRRING METHOD, CELL, AND MEASURING APPARATUS USING THE SAME

(75) Inventors: Akihito Kamei, Kyoto (JP); Fumihisa Kitawaki, Ehime (JP); Tatsurou Kawamura, Kyoto (JP); Hiroshi Nakayama, Osaka (JP); Nobuyuki Shigetou, Kyoto (JP)

(73) Assignee: Panasonic Corporation, Osaka (JP)

( * ) Notice: Subject to any disclaimer, the term of this patent is extended or adjusted under 35 U.S.C. 154(b) by 1066 days.

(21) Appl. No.: 10/588,546

(22) PCT Filed: Mar. 23, 2005

(86) PCT No.: PCT/JP2005/005260

§ 371 (c)(1),
(2), (4) Date: Aug. 7, 2006

(87) PCT Pub. No.: WO2005/090998

PCT Pub. Date: Sep. 29, 2005

(65) Prior Publication Data

US 2007/0172961 A1    Jul. 26, 2007

(30) Foreign Application Priority Data

Mar. 23, 2004  (JP) .............................. 2004-084353

(51) Int. Cl.
*G01N 1/00* (2006.01)
*G01N 33/00* (2006.01)
*G01N 21/00* (2006.01)
*G01N 15/06* (2006.01)
*G01N 33/53* (2006.01)

(52) U.S. Cl. ................ 436/174; 422/57; 422/68.1; 422/73; 422/82.05; 435/7.1

(58) Field of Classification Search ............ None
See application file for complete search history.

(56) References Cited

U.S. PATENT DOCUMENTS 5,482,863 A    1/1996    Knobel (Continued)

FOREIGN PATENT DOCUMENTS

EP    0 644 426    9/1993

(Continued)

OTHER PUBLICATIONS

Search Report dated Apr. 25, 2007.

*Primary Examiner*—Jill Warden
*Assistant Examiner*—Neil Turk
(74) *Attorney, Agent, or Firm*—McDermott Will & Emery LLP

(57) ABSTRACT

A method capable of stirring a liquid sample and a reagent promptly and easily includes the following steps (A) and (B). In step (A), using a cell including: a liquid sample retaining section having a plurality of particles; and a liquid sample supply inlet, a liquid sample containing an analyte is supplied from the liquid sample supply inlet to the liquid sample retaining section. In step (B), the liquid sample and a specific binding substance capable of specifically binding to the analyte are stirred by the movement of the particles caused by the flow of the liquid sample in the cell resulting from the supply of the liquid sample, to obtain a liquid mixture. The electric charge of at least the surface of the particles and the electric charge of the specific binding substance have the same polarity in the liquid mixture.

12 Claims, 10 Drawing Sheets

U.S. PATENT DOCUMENTS

| | | |
|---|---|---|
| 5,482,864 A | 1/1996 | Knobel |
| 2002/0182640 A1 | 12/2002 | Saito et al. |
| 2003/0170145 A1* | 9/2003 | Smith et al. ............ 422/68.1 |
| 2004/0032590 A1 | 2/2004 | Kawamura et al. |

FOREIGN PATENT DOCUMENTS

| | | |
|---|---|---|
| EP | 1 355 144 | 10/2003 |
| EP | 1359404 | 11/2003 |
| EP | 1 484 598 | 12/2004 |
| JP | 3-46566 A | 2/1991 |
| JP | 3-214049 A | 9/1991 |
| JP | 4-363665 A | 12/1992 |
| JP | 7-174763 A | 7/1995 |
| JP | 2000-254472 A | 9/2000 |
| JP | 2002-311034 A | 10/2002 |
| JP | 2003-254877 A | 9/2003 |
| WO | WO 02/072510 | 9/2002 |
| WO | WO 03/010513 A1 | 2/2003 |

* cited by examiner

STIRRING METHOD, CELL, AND MEASURING APPARATUS USING THE SAME

RELATED APPLICATIONS

This application is the U.S. National Phase under 35 U.S.C. §371 of International Application No. PCT/JP2005/005260, filed on Mar. 23, 2005, which in turn claims the benefit of Japanese Application No. 2004-084353, filed on Mar. 23, 2004, the disclosures of which Applications are incorporated by reference herein.

TECHNICAL FIELD

The present invention relates to a method for stirring a liquid sample and a reagent which is used, for example, in clinical tests that make chemical analyses of liquid samples, such as blood and urine. The present invention further pertains to a cell preferable for this stirring method and to a measuring apparatus using this cell.

BACKGROUND ART

In test devices such as immunochemical analyzers and biochemical analyzers, a liquid sample and a reagent are stirred, in order to effectively cause reaction in a container, such as an analytical cell, and to maintain measurement accuracy.

As conventional techniques for such stirring, for example, rotating a magnetic rotor by means of a magnetic stirrer (Patent document 1), vibrating stirring blades by using a piezo element as the driving gear (Patent document 2), and rotating a reaction cassette to transport liquid by gravity into contact with a flow disrupting means provided in the reaction cassette for stirring have been proposed.

Patent document 1: JP 3-214049 A
Patent document 2: JP 4-363665 A
Patent document 3: JP 3-46566 A

DISCLOSURE OF THE INVENTION

Problem to be Solved by the Invention

However, such conventional techniques shown in Patent documents 1 to 3 need to perform a stirring step by using a driving gear to operate a stirring mechanism, independently of and in addition to a step of injecting a liquid sample or a reagent into a reaction system.

Specifically, after the injection of a liquid sample or a reagent into the reaction system, the following manipulative steps are necessary. For example, Patent document 1, the magnetic rotor needs to be rotated by a magnetism generator. In Patent document 2, the stirring blades need to be vibrated by the piezo element. Further, in Patent document 3, the reaction cassette needs to be rotated, using, for example, a stepping motor as the driving gear.

Accordingly, conventional stirring techniques have a problem in that an additional driving gear is necessary for stirring, thereby resulting in complicated structure of a test device including a stirring device.

Also, the stirring step needs to be performed independently of the step of injecting a liquid sample or a reagent into the reaction system. Hence, there is another problem in that it takes a considerably long time, from the injection of the liquid sample and the reagent into the reaction system, to make an accurate measurement of reaction commensurate with the concentration of the liquid sample and the reagent in the reaction system.

These conventional problems are particularly associated with POCT (Point of Care Testing) devices of quantification type, which are required to provide prompt and accurate measurements at test sites. In consideration of the prospect that POCT devices of quantification type will increasingly become more popular, these problems need to be resolved promptly.

Under such circumstances, it is therefore an object of the present invention to solve the above-mentioned conventional problems and provide a method, a cell and a measuring apparatus for stirring a liquid sample and a reagent in a prompt and easy manner with a simple structure.

Means for Solving the Problem

In order to solve the conventional problems as described above, the present invention provides a method for stirring a liquid sample containing an analyte and a specific binding substance including the steps of:

(A) using a cell including a liquid sample retaining section having a plurality of particles and a reagent, and a liquid sample supply inlet, supplying a liquid sample containing an analyte from the liquid sample supply inlet to the liquid sample retaining section, and (B) stirring the liquid sample and the reagent by the movement of the particles caused in the liquid sample retaining section by the flow of the liquid sample resulting from the supply of the liquid sample, to obtain a liquid mixture containing the liquid sample, the reagent and the particles.

The present invention also provides
a cell including: a liquid sample retaining section having a plurality of particles and a reagent; and a liquid sample supply inlet,
wherein the particles are retained in the liquid sample retaining section in such a manner as to be movable by the flow of a liquid sample supplied from the liquid sample supply inlet into the liquid sample retaining section, and
the liquid sample and the particles are stirred by the movement of the particles.

The present invention further provides a measuring apparatus including:
a cell holder that holds the above-mentioned cell further including a light entrance for allowing light to enter the liquid sample retaining section, and a light exit for allowing the light to exit from the liquid sample retaining section;
a liquid sample supply unit for supplying the liquid sample to the liquid sample retaining section through the liquid sample supply inlet;
a light source for emitting light to the light entrance of the cell; and
a light detector for detecting the light that has exited from the light exit of the cell,
wherein an analyte in the liquid sample is measured based on the light detected by the light detector.

Further, the present invention provides a measuring method further including, in addition to the above-mentioned stirring method, by using a cell including a light entrance for allowing light to enter the liquid sample retaining section, and a light exit for allowing the light to exit from the liquid sample retaining section, the steps of:

(C) allowing a light enter into the liquid sample retaining section through the light entrance;

(D) detecting the light exited to outside of the liquid sample retaining section through the light exit; and (E) measuring an analyte in the liquid sample based on the light detected after the particles in the liquid mixture are settle down.

EFFECT OF THE INVENTION

According to the stirring method, cell and measuring apparatus of the present invention, it is possible to stir a liquid sample and a reagent in a prompt and easy manner with a simple structure.

BEST MODE FOR CARRYING OUT THE INVENTION

Figure 1:
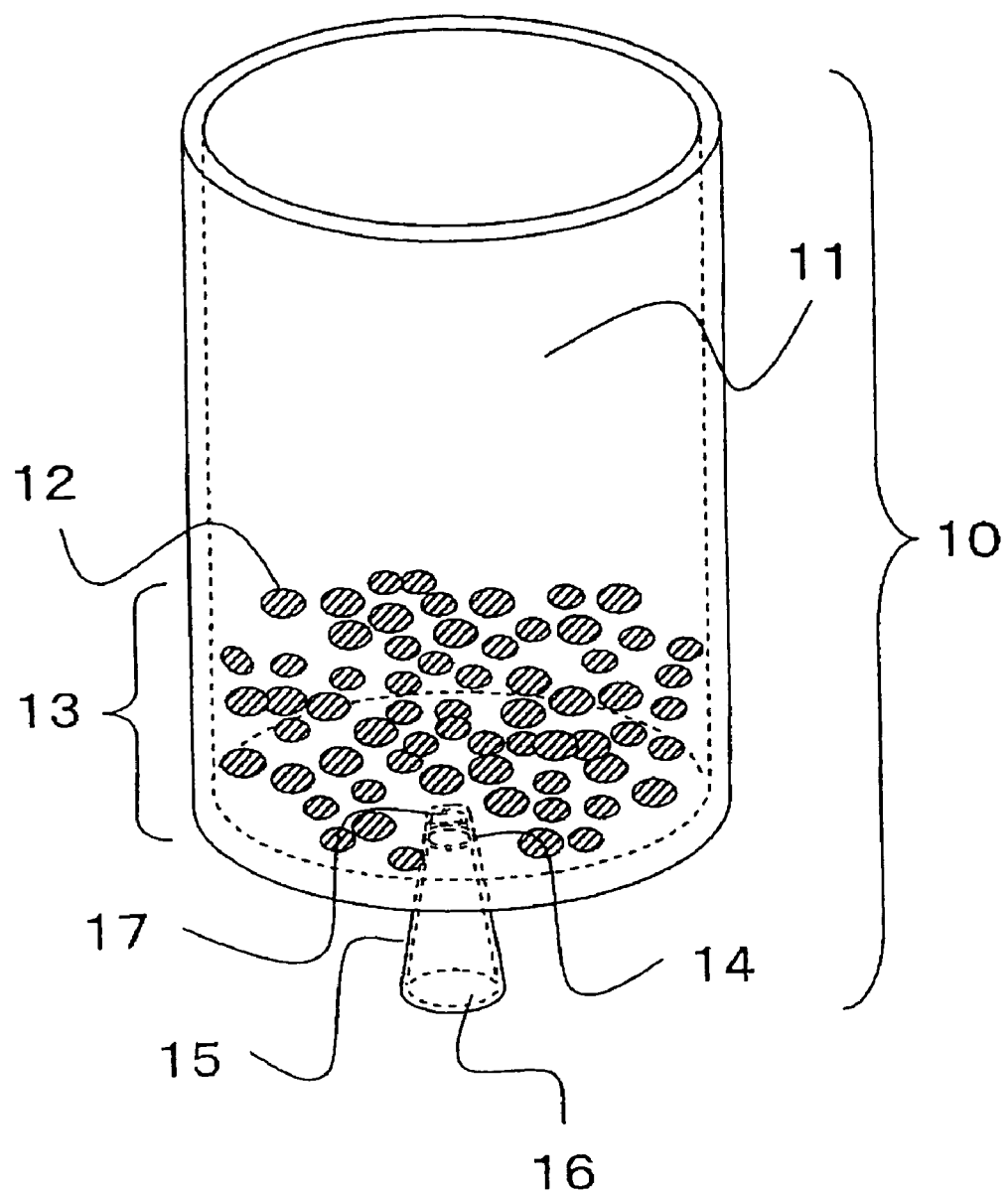
FIG. 1 is a perspective view showing the structure of a stirring device according to Embodiment 1 of the present invention.

The present invention relates a method for stirring a liquid sample containing an analyte and a reagent. This method includes the following steps (A) and (B). In the step (A), using a cell including: a liquid sample retaining section having a plurality of particles and the reagent; and a liquid sample supply inlet, a liquid sample containing an analyte is supplied from the liquid sample supply inlet to the liquid sample retaining section. In the step (B), the liquid sample and a reagent are stirred by the movement of the particles caused in the liquid sample retaining section by the flow of the liquid sample in the cell resulting from the supply of the liquid sample, to obtain a liquid mixture containing the liquid sample, the reagent and the particles.

A cell of the present invention includes a liquid sample retaining section having a plurality of particles and a reagent and a liquid sample supply inlet, wherein the particles are retained in the liquid sample retaining section in such a manner as to be movable by the flow of a liquid sample supplied from the liquid sample supply inlet into the liquid sample retaining section, and the liquid sample and the particles are stirred by the movement of the particles.

By the above manner, by the flow of the liquid sample from the liquid sample supply inlet into the liquid sample retaining section, movement of liquid can be generated in the liquid sample retaining section. A plurality of the particles retained in the liquid sample retaining section move along with the movement of the liquid, thereby the liquid sample and the reagent are stirred and mixed uniformly. And, the time required to evenly mix a liquid sample with a reagent can be shorten, compared with the stirring techniques used in conventional test devices for detecting homogeneous reaction, in which the step of introducing a liquid sample and a reagent into the reaction system and the step of stirring them are performed separately and independently. Therefore, application of the stirring method of the present invention to test devices for detecting homogeneous reaction makes it possible to shorten the time required to measure reaction between a liquid sample and a reagent.

Also, since the stirring step is performed by utilizing the flow of a liquid sample created by the introduction of the liquid sample into the container, there is no need to use an additional driving gear for stirring, thereby making the structure of the measuring apparatus simple.

As described above, according to the present invention, a liquid sample and a reagent can be stirred with an apparatus having a simplified structure speedy and simply.

In the stirring method, cell and measuring apparatus of the present invention, exemplary liquid samples include water-soluble liquid samples and colloidal liquids containing colloidal particles that are capable of being suspended in water. More specifically, examples include body fluids, such as urine, blood, blood plasma, blood serum, saliva, interstitial fluid, sweat, and tears, or aqueous solutions dissolving biological components.

The reagent may be any material containing a substance that is reactive to an analyte in a liquid sample. Examples for the substance that is reactive to an analyte include: a ferment; an immunoreactive substance causing an antigen-antibody reaction with an analyte; and a substance causing a ligand receptor reaction with an analyte. Among them, it is preferred to use a specific binding substance that is capable of specifically binding to an analyte for the substance that is reactive to an analyte. As the specific binding substance, an immunoreactive substance and a substance causing a ligand receptor reaction with an analyte are exemplified.

It is particularly preferred to use an antibody, since it is capable of specifically binding to a low molecular compound, a polymer compound such as protein, a bacterium, a virus, etc., and is therefore applicable extensively.

Also, a reagent used for optically measuring reaction is preferable.

In the present invention, the particles are not necessarily spherical but in a desired shape. The particles may be any particles that are insoluble in water, have a specific gravity greater than 1, and can settle down in a liquid sample. It is also preferred to use particles that are floated and moved easily in a liquid sample by the flow caused by a water pressure of about −1 at. to +1 at. and then settle down promptly.

Exemplary materials for the particles include glass, sea sand, silica, metal, and resins such as polystyrene, polyethylene, acryl and polypropylene. The size of the particles is preferably approximately 400 to 700 µm. Among them, it is preferred to use glass particles or sea sand, having a particle size of approximately 400 to 700 µm.

It is preferred that the particles and the specific binding substance are adjusted such that an electric charge of at least the surface of the particles and the electric charge of the specific binding substance have the same polarity in the liquid mixture of the liquid sample and the reagent.

According to such constitution, upon the mixing of the particles with the liquid sample, the particles and the specific binding substance electrostatically repel one another, thereby facilitating the separation of the specific binding substance from the particles, the dissolution of the specific binding substance into the liquid sample, and the mixing of the specific binding substance with the liquid sample.

Specifically, when the particles carry protein as the specific binding substance, the particle surface may be provided with, for example, functional groups that are capable of maintaining an electric charge of a certain polarity in the range of about pH 4 to 9.

For example, suppose that particles having amino groups at the surface are used as the above-mentioned particles and that an antibody is used as the specific binding substance. The amino groups are positively charged in the range of about pH 4 to 9. Thus, on the assumption that the isoelectric point pI of the antibody is 6.5 (note that the isoelectric point pI of a common antibody is 6 to 8), if a positively charged antibody (its molecule is positively charged as a whole) is carried on the particles at a pH of less than 6.5 (preferably about pH 4.5 to 5.5), the positively charged antibody and the positive electric charge of the particle surface repel one another. As a result, the adsorption of the antibody on the particles can be prevented.

Meanwhile, suppose that a protein whose isoelectric point is on the acidic side and which is negatively charged around neutrality is used around neutrality (e.g., pH 7.4) as the specific binding substance. Then, particles having sulfonic acid groups or carboxyl groups as the functional groups at the surface may be used. In this case, the functional groups and the protein are both negatively charged and therefore repel one another.

Also, in the present invention, it is preferred that a buffer be contained in the container so as to cause a pH change such that the electric charge of the particles and the electric charge of the specific binding substance repel one another upon the mixing of the liquid sample with the particles.

According to such constitution, the pH can be easily adjusted such that the particles and the specific binding substance electrostatically repel one another upon the mixing. Also, since the pH can be stabilized, the electrostatic repulsion of the particles and the specific binding substance can be reproduced in a reliable manner.

The particles may be coated with a reagent such that the reagent is dissolved in a liquid sample supplied from the liquid sample supply inlet into the liquid sample retaining section. In this case, the reagent may be carried on entire surface of each particle or the reagent may be carried on only a part of the surface of each particle.

According to such constitution, due to the contact between the reagent-coated particles and the liquid sample, the reagent separates from the particles by dissolving in the liquid sample.

Upon the dissolution, the concentration of the specific binding substance may be gradient changing from the particle surface toward the outer side (i.e., as you go further away from the vicinity of the particle surface). This gradient concentration becomes higher in the vicinity of the particles to reduce the dissolution of the reagent. However, the movement of the particles in the liquid makes it possible to prevent the reagent from getting dissolved at a remarkably high concentration in the vicinity of the particles. As above, it is possible to suppress the prevention of the reagent dissolution and to promote the dissolution of the reagent into the liquid sample.

Further, the movement of the particles creates turbulent flows, thereby stirring the liquid sample and the specific binding substance serving as a reagent. It is thus possible to obtain a liquid mixture in which the liquid sample and the reagent are evenly dispersed.

In the present invention, when a reagent is carried on the particles, the reagent may be carried on the surface of each particle such that the particles may be individually and separately covered with the reagent or the plurality of the particles may be totally covered with the reagent.

It is preferred that the reagent be individually and separately carried on the surface of each particle. This is because the provision of the reagent on each particle can increase the contact area between the reagent and the liquid sample, thereby ensuring the flowability of the particles in the resultant liquid mixture, and facilitating the dissolution of the reagent.

Also, the reagent carried on the particles is preferably in a dry state. The reagent can be dried by means of air-drying, freeze-drying, and the like, but it is preferred to employ freeze-drying in terms of the solubility and activity maintenance of the reagent.

Reagent-coated particles can be individually and separately provided, for example, by freeze-drying a suitable amount of a reagent on one particle. Alternatively, a mixture of a reagent and a plurality of particles may be freeze-dried and then pulverized into individual reagent-coated particles. The latter method is inferior to the former method in terms of dissolution efficiency, since part of the reagent may not be carried on the particles. However, the latter method is superior to the former method from the viewpoint of the ease with which the reagent is carried on the particles.

Also, in the present invention, it is preferred that a substance (adsorption inhibiting substance) inhibiting the specific binding substance from adsorbing to the particles be provided on the surface of the particles.

Such constitution prevents the specific binding substance from non-specifically adsorbing to the particles, thereby preventing the reagent from not reacting with a liquid sample. Thus, the specific binding substance can be more effectively reacted with the analyte. Exemplary substances that inhibit the reagent from adsorbing to the particles include silicon and proteins which do not contribute to the reaction between the liquid sample and the reagent.

It is preferred that the substance inhibiting the reagent from adsorbing to the particles also inhibit an analyte in a liquid sample from adsorbing to the particles. The substance inhibiting the specific binding substance from adsorbing to the particles is preferably provided so as to cover the surfaces of the particles. Further, preferably, this substance does not contribute to the reaction between the liquid sample and the reagent.

For example, in using an immunoassay reagent, casein, bovine serum albumin, gelatin, and the like can be used as the substance inhibiting the specific binding substance from adsorbing to the particles. If glass particles are incubated, for example, in a solution containing 1% by weight of casein for more than 1 hour, the casein can be adsorbed on the particles, so that the particle surface can be inactivated.

In the present invention, it is also preferred that a substance (reaction inhibiting substance) that adsorbs a substance inhibiting the reaction between the liquid sample and the specific binding substance be provided on the surface of the particles.

Such constitution can eliminate a substance inhibiting the reaction between the liquid sample and the specific binding substance from a solution of a mixture of the liquid sample and the reagent, thereby facilitating the reaction between the liquid sample and the specific binding substance more effectively. Exemplary substances that adsorb a substance inhibiting the reaction between the liquid sample and the reagent include receptor molecules of the reaction-inhibiting substance and immunoreactive substances capable of specifically binding to the reaction-inhibiting substance.

It is preferred that the substance that adsorbs a substance inhibiting the reaction between the liquid sample and the reagent be provided so as to cover the surface of the particles. Further, preferably, this substance does not contribute to the reaction between the liquid sample and the specific binding substance.

For example, in the case of using glass particles as the particles, in order to provide a substance that adsorbs a substance inhibiting the reaction between the liquid sample and the specific binding substance around the glass particles, the glass particles may be incubated in a solution containing such an adsorbent, in order to cause the glass particles to adsorb the adsorbent.

For example, in the case of the liquid sample being human blood, blood plasma, blood serum, urine, or the like, when an immunoassay reagent containing an animal-derived antibody is reacted with an analyte in the liquid sample, the liquid sample contains a human-derived antibody to the animal-derived antibody. This human-derived antibody inhibits the reaction between the analyte in the liquid sample and the reagent. Such instances are known in the art.

In this case, glass particles may be incubated in a solution containing approximately 0.1 mg/ml of an antibody to the human-derived antibody for more than 1 hour, in order to cause the glass particles to adsorb the antibody to the human-derived antibody.

If the human-derived antibody, which is an inhibitor, is bound to the antibody to the human-derived antibody provided on the glass particles and, the glass particles are allowed to settle down, the human-derived antibody (inhibitor) can be localized in the container. This can limit the binding of the human-derived antibody to the animal-derived antibody with the animal-derived antibody contained in the reagent, thereby suppressing the inhibition of the reaction between the animal-derived antibody in the reagent and the analyte in the liquid sample by the human-derived antibody to the animal-derived antibody.

It is also known that when a blood sample is measured for its CRP (C-reactive protein) content, which increases in the case of a bacterial infectious disease, etc., a rheumatoid factor exerts an adverse effect on the measurement. However, the adverse effect of the rheumatoid factor can be eliminated in the same manner as the above case, by causing the particles to adsorb an antibody that binds to the rheumatoid factor.

With respect to the container material constituting the cell of the present invention, there are no particular limitations as long as it is insoluble in a liquid sample and a reagent; however, the material is preferably transparent to the extent that the inside can be viewed visually. If the inside can be viewed visually, the stirring degree of the liquid sample and the reagent in the container can be readily checked. Thus, in the event of trouble, measures can be taken promptly, and the reaction between the liquid sample and the reagent can be determined by visual observation.

Specifically, such examples include glass, polystyrene, polyethylene, acryl, polypropylene, etc.

Further, the container is preferably formed of a material to which a liquid sample and a reagent are unlikely to adsorb non-specifically. Alternatively, the container may be formed of a material that is treated so as to prevent the non-specific adsorption of a liquid sample and a reagent.

For example, in using reagents containing protein, peptide, DNA or the like, or liquid samples containing protein, peptide, DNA or the like as the analyte, it is preferred to use polypropylene, because protein, peptide and DNA are unlikely to adsorb unspecifically on polypropylene.

Also, when the container is formed of glass or polystyrene to which protein, peptide, DNA and the like are apt to adsorb relatively non-specifically, the inner surface of the container may be coated with a material that does not contribute to or inhibit the reaction between the liquid sample and the specific binding substance.

Exemplary materials used for such coating include silicon and protein that does not contribute to the reaction between the liquid sample and the reagent.

Also, in the cell of the present invention, it is preferred to dispose the liquid sample supply inlet such that the liquid sample introduced from the liquid sample supply inlet into the container moves along the inner face of the wall of the container.

It is particularly preferred to provide the liquid sample supply inlet such that the flow of the liquid sample supplied into the container becomes a flow circulating along the inner face of the wall of the container. This makes it possible to effectively cause a flow of the liquid sample in the container, facilitate the floating and movement of the particles, and enhance the effects of stirring/mixing the liquid sample and the reagent.

Also, it is preferred that the diameter of the opening located outside the liquid sample supply inlet be greater than the diameter of the opening located inside the liquid sample supply inlet.

This constitution can increase the speed of the liquid sample flowing into the container from the outside of the container, thereby making it possible to cause a faster flow of the liquid sample in the container. This constitution can further facilitate the floating and movement of the particles, thereby enhancing the effects of stirring/mixing the liquid sample and the reagent.

Also, in the present invention, it is preferred that the container be equipped with a light entrance for allowing light to enter the liquid sample retaining section and a light exit for allowing the light to exit from the liquid sample retaining section.

This constitution eliminates the need to transfer the liquid mixture of the liquid sample and the reagent into another optical cell for optical measurement. As a result, the reaction caused by stirring can be promptly measured spectroscopically, and the measurement time can be further shortened. When measuring a transitional change of reaction, in particular, the transitional change can be captured in a reliable manner with little time loss. Further, since no mechanism is necessary for transferring the liquid mixture into another optical cell, the constitution of the measuring apparatus can be simplified.

The light entrance and the light exit are substantially flat and formed of a material that is optically substantially transparent. It is preferred that the plane of the light exit be disposed so as to be substantially parallel to the plane of the light entrance. In this case, the light having entered the liquid sample retaining section from the light entrance and passed through the liquid mixture of the liquid sample and the reagent in the liquid sample retaining section can be allowed to exit from the liquid sample retaining section through the light exit. Accordingly, it is possible to provide a measuring apparatus with an optical measurement mechanism preferable for the measurement of absorbance or turbidity.

Also, the plane of the light exit may be disposed so as to be substantially perpendicular to the plane of the light entrance. In this case, the light having entered the liquid sample retaining section from the light entrance and scattered in the liquid mixture of the liquid sample and the reagent in the c liquid sample retaining section, or the fluorescence generated in the liquid mixture by the light having entered the liquid sample retaining section from the light entrance, can be allowed to exit from the liquid sample retaining section through the light exit. Accordingly, it is possible to provide a measuring apparatus with an optical measurement mechanism preferable for the measurement of scattered light intensity or fluorescence.

The optically substantially transparent material that constitutes the light entrance and the light exit is preferably quartz glass or polystyrene, for example. Such materials have good transparency in the visible region, and are therefore preferable for optical measurement in the visible region.

A measuring apparatus in accordance with the present invention includes: a cell holder that holds the above-mentioned cell; a liquid sample supply unit for supplying the liquid sample to the liquid sample retaining section through the liquid sample supply inlet of the cell; a light source for emitting light to the light entrance of the cell; and a light detector for detecting the light that has exited from the light exit of the cell. This measuring apparatus measures an analyte contained in the liquid sample based on the light detected by the light detector.

It is preferred that the liquid sample supply unit is a liquid sample sucking means. For the liquid sample sucking means, a plunger, a syringe, etc are exemplified.

Further, a measuring method in accordance with the present invention further including, in addition to the above-mentioned stirring method, by using a cell including a light entrance for allowing light to enter the liquid sample retaining section, and a light exit for allowing the light to exit from the liquid sample retaining section, the steps of:

(C) allowing a light enter into the liquid sample retaining section through the light entrance;

(D) detecting the light exited to outside of the liquid sample retaining section through the light exit; and (E) measuring an analyte in the liquid sample based on the light detected after the particles in the liquid mixture settle down.

Referring now to drawings, embodiments of the present invention are described more specifically, but the present invention is not to be construed as being limited thereto.

Embodiment 1

FIG. 1 is a schematic perspective view showing the structure of a stirring device using the cell according to Embodiment 1 of the present invention. As illustrated in FIG. 1, a stirring device 10 of this embodiment includes a cylindrical container 11 with a bottom. A liquid sample retaining section 13 of the container 11 contains reagent-coated particles 12, which are coated with an immunoassay reagent including an immunoreactive substance (specific binding substance) that causes an antigen-antibody reaction with an analyte contained in a liquid sample.

These particles 12 are retained in the liquid sample retaining section 13 in such a manner as to be movable by the flow of liquid, such as a liquid sample, in the liquid sample retaining section 13.

Also, a liquid sample supply inlet through which a liquid sample is introduced is composed of an opening 14 of the container 11 and a pipe 15 penetrating the wall of the container 11 through the opening 14. The diameter of an opening 16 of the pipe 15 located outside the container 11 is greater than the diameter of an opening 17 of the pipe 15 located inside the container 11.

Since the container 11 is made of transparent polypropylene, the inside of the container 11 can be viewed visually. The particles used for preparing the reagent-coated particles 12 are particles obtained by coating the surfaces of glass particles of approximately 550 µm in size with polylysine to make them positively charged (polylysine-coated particles).

A reagent is provided on the particles as follows. A solution containing an antibody with an isoelectric point of 6.5, which serves as an immunoassay reagent, is mixed with a plurality of polylysine-coated glass particles, to obtain a mixture. This mixture is freeze-dried at pH 7.5, and the resultant freeze-dried mixture is pulverized into individual reagent-coated particles.

Also, a citric acid buffer, which is prepared such that the pH will be maintained at 5.0 upon the mixing of a liquid sample and the reagent-coated particles, is dropped in the liquid sample retaining section 13.

Next, the operations of the stirring device 10 of this embodiment are described below.

First, urine is introduced as a liquid sample from the opening 16, to supply the liquid sample into the container 11 through the opening 14 of the container 11. This supply causes a flow of the liquid in the container 11, thereby floating and moving the reagent-coated particles 12 in the liquid sample retaining section 13. This movement of the particles 12 dissolves the immunoassay reagent and mixes and stirs the liquid sample, the immunoassay reagent and the citric acid buffer in the container 11.

According to this embodiment, by introducing a liquid sample into the container 11 from the opening 14 of the container 11, a liquid flow can be created in the container 11. This liquid flow moves the plurality of reagent-coated particles 12 in the container 11, thereby dissolving the immunoassay reagent and mixing and stirring the liquid sample, the immunoassay reagent and the citric acid buffer. As a result, a homogeneous liquid mixture can be obtained.

Accordingly, the time required to homogenize a liquid sample and a reagent can be shortened, in comparison with conventional stirring devices which perform the step of introducing a liquid sample and a reagent into a reaction system and the step of stirring them separately and independently.

Further, since the particles are coated with the immunoassay reagent, the movement of the particles can prevent a rise in the concentration gradient (i.e., the concentration gradient of the dissolved reagent in the vicinity of the reagent-coated particles) of the immunoassay reagent in the vicinity of the particles caused by the dissolution of the reagent upon contact with the liquid sample. Also, the dissolution of the reagent carried on the particles into the liquid sample can be facilitated.

Furthermore, since the specific binding substance is carried around the particles, the surface area on which it is carried can be enlarged, so that the specific binding substance can be carried in larger amounts, in comparison with the specific binding substance carried on the container wall and the like.

Also, when the reagent-coated particles 12 are prepared as in this embodiment and the pH is maintained at 5.0 upon the mixing with the liquid sample, the antibody (specific binding substance) in the immunoassay reagent becomes positively charged because the isoelectric point of the antibody is 6.5, and the particle surface becomes positively charged because the polylysine on the particle surface has a positive electric charge. Consequently, the particles and the antibody carried on the particles electrically repel one another, thereby facilitating the separation of the antibody from the particles.

Also, since the stirring step can be performed by utilizing the liquid flow caused by the introduction of the liquid sample into the container 11, there is no need to provide an additional driving gear for stirring, which makes the structure simple.

As described above, according to this embodiment, a liquid sample and a reagent can be stirred in a prompt and easy manner with a simple structure.

Also, because the diameter of the opening 16 of the pipe 15 located outside the container 11 is greater than the diameter of the opening 17 of the pipe 15 located inside the container 11, liquid flows into the container 11 from the outside of the container 11 at a high speed. Therefore, a faster liquid flow can be created in the container 11. This makes it possible to promote the floating and movement of the reagent-coated particles 12 and enhance the effects of mixing/stirring the liquid sample and the immunoassay reagent.

Embodiment 2

Figure 2:
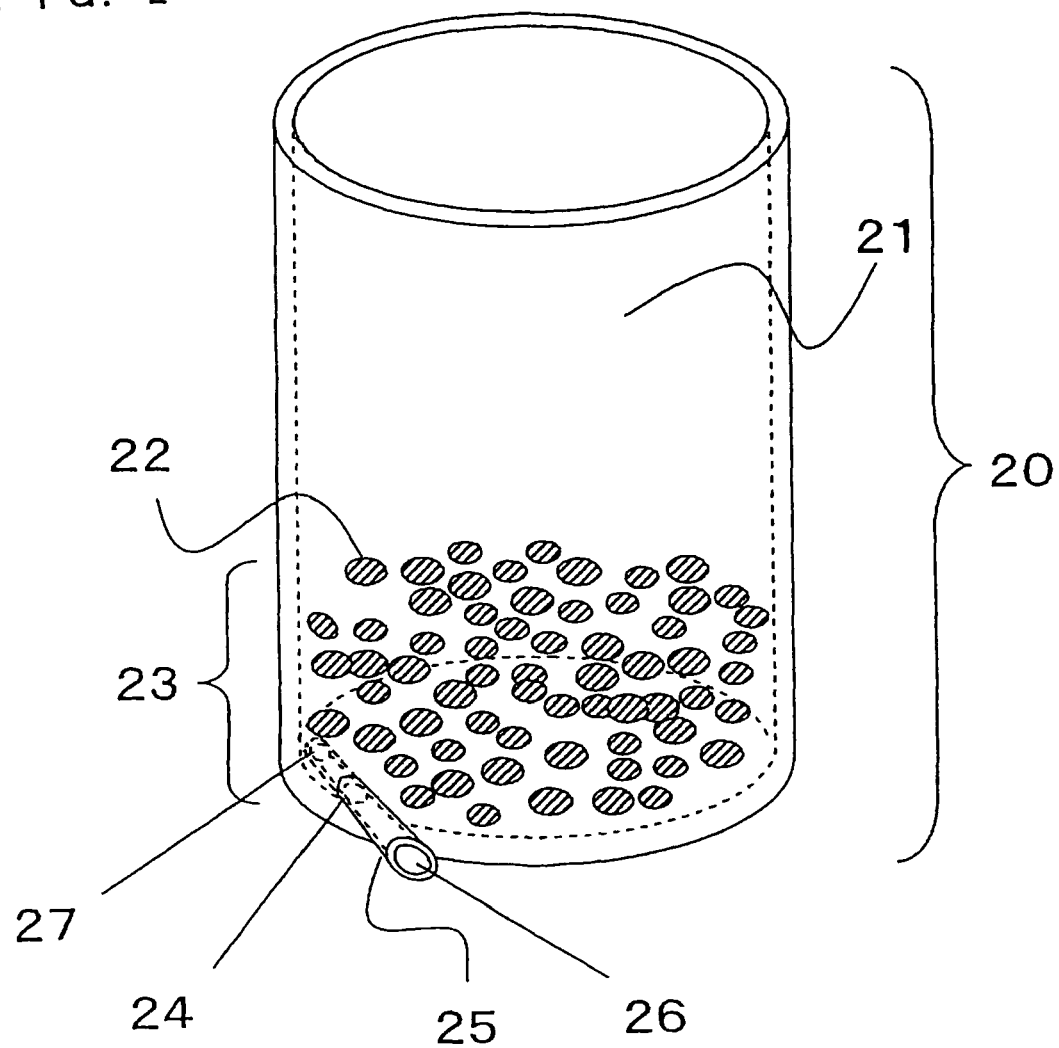
FIG. 2 is a perspective view showing the structure of a stirring device according to Embodiment 2 of the present invention.

Referring now to FIG. 2, a stirring device using the cell according to Embodiment 2 of the present invention is described. FIG. 2 is a perspective view showing the structure of a stirring device according to this embodiment.

A stirring device 20 of this embodiment is the same as the measuring apparatus of Embodiment 1, except that a pipe 25 is disposed at a different position.

A liquid sample retaining section 23 of a container 21 contains reagent-coated particles 22, and the diameter of an opening 26 of the pipe 25 located outside the container 21 is greater than the diameter of an opening 27 of the pipe 25 located inside the container 21. However, unlike Embodiment 1, the pipe 25 is provided such that a liquid sample introduced into the container 21 from an opening 24 moves along the inner face of the wall of the container 21, as illustrated in FIG. 2.

This embodiment can produce essentially the same action and effect as those of Embodiment 1. In addition, the liquid sample introduced from the opening 24 forms a flow circulating along the inner face of the wall of the container 21. The resultant circulating flow can cause a liquid flow in the container 21 effectively, thereby facilitating the floating and movement of the reagent-coated particles 22. This can further enhance the effect of dissolving the reagent in the liquid sample and the effect of stirring/mixing the liquid sample and the reagent, in comparison with Embodiment 1.

Embodiment 3

Figure 3:
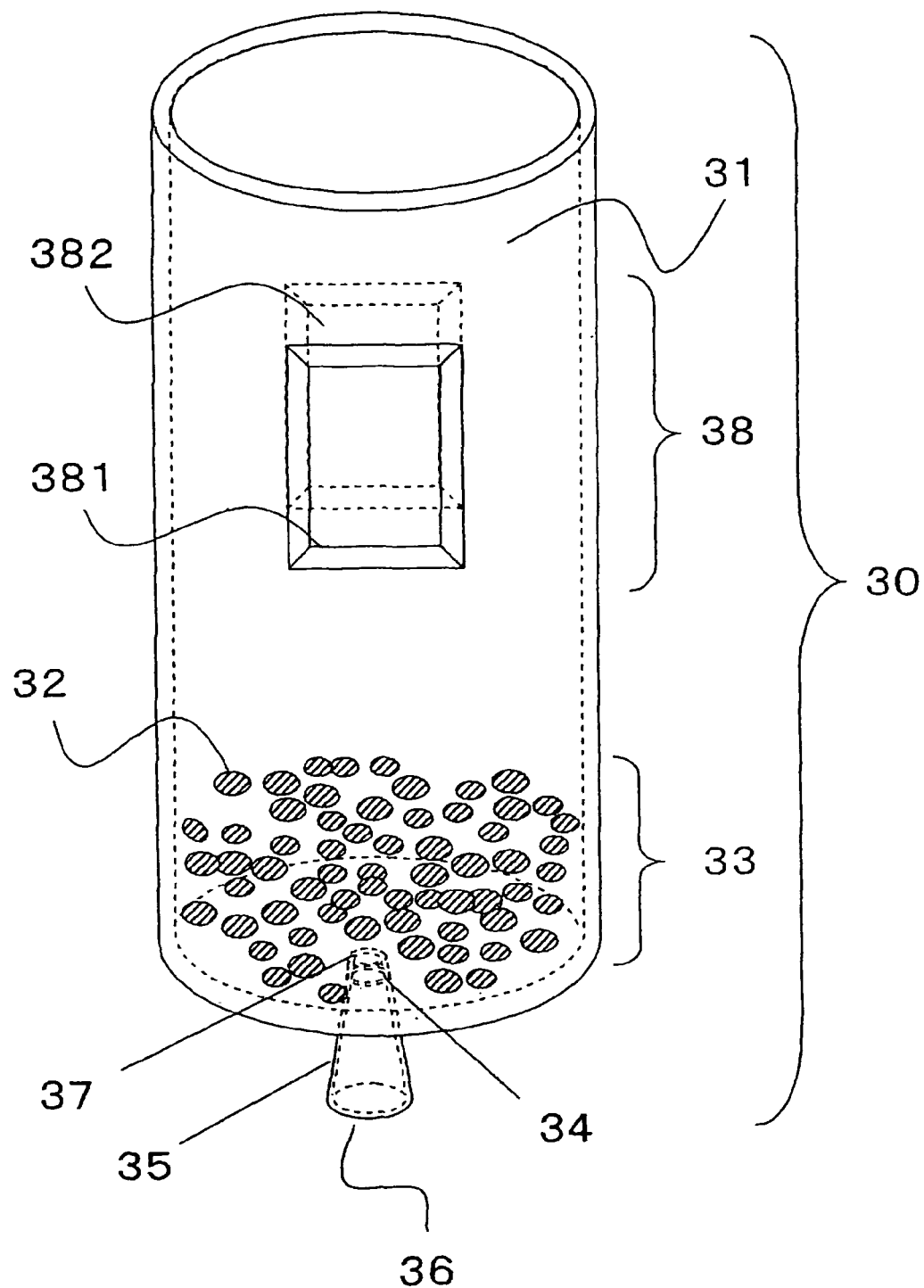
FIG. 3 is a perspective view showing the structure of a stirring device according to Embodiment 3 of the present invention.

Referring now to FIG. 3, a stirring device using the cell according to Embodiment 3 of the present invention is described. FIG. 3 is a perspective view showing the structure of a stirring device according to this embodiment.

A stirring device 30 according to this embodiment is the same as the stirring device of Embodiment 1, except that it has a light entrance for allowing light to enter a container 31 and a light exit for allowing the light to exit from the container 31.

A liquid sample retaining section 33 of the container 31 contains reagent-coated particles 32, and a liquid sample supply inlet is composed of an opening 34 of the container 31 and a pipe 35 penetrating the wall of the container 31 through the opening 34. The diameter of an opening 36 of the pipe 35 located outside the container 31 is greater than the diameter of an opening 37 of the pipe 35 located inside the container 31.

The container 31 has, in its walls, an optical measurement section 38 including an incident light window 381, which serves as the light entrance, and a transmitted light window 382, which serves as the light exit.

The incident light window 381 and the transmitted light window 382 are substantially flat and made of polystyrene which is a material that is optically transparent, and the plane of the transmitted light window 382 is disposed so as to be substantially parallel to the plane of the incident light window 381.

This embodiment can produce essentially the same action and effect as those of Embodiment 1, and in addition, it enables easy and reliable optical measurements.

A liquid sample is supplied into the container 31. After the lapse of a predetermined time therefrom, light is irradiated substantially perpendicularly to the incident light window 381 from a light source (not shown). The light enters the container 31 from the incident light window 381, passes through a liquid mixture of the liquid sample and a reagent in the container 31, and exits from the container 31 through the transmitted light window 382. This light is then received by a light receiving section (not shown). Based on the intensity of the light received by the light receiving section, the absorbance or turbidity of the liquid mixture is determined, whereby the reaction between the liquid sample and the reagent can be measured.

As described above, the stirring device 30 of this embodiment has the optical measurement section 38 including the incident light window 381 serving as the light entrance and the transmitted light window 382 serving as the light exit. Therefore, in performing an optical measurement, there is no need to transfer the liquid mixture from the container 31 into another optical cell, thereby enabling a prompt spectroscopic measurement of the reaction caused by stirring. As a result, the measurement time can be further shortened. When measuring a transitional change of reaction, in particular, the transitional change can be captured in a reliable manner with little time loss. Further, since no mechanism is necessary for transferring the liquid mixture into an optical cell, the constitution of the measuring apparatus can be simplified.

Embodiment 4

Figure 4:
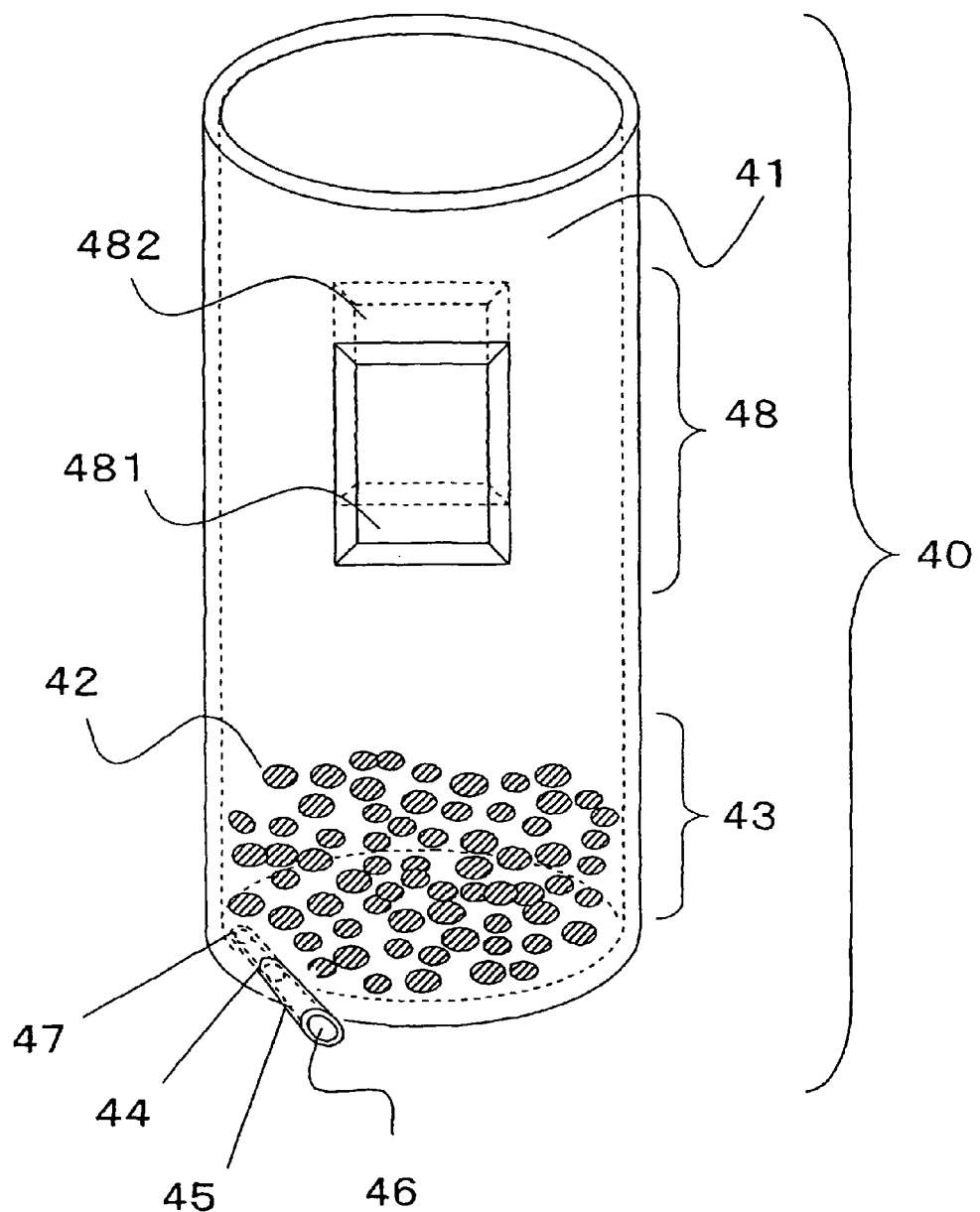
FIG. 4 is a perspective view showing the structure of a stirring device according to Embodiment 4 of the present invention.

Referring now to FIG. 4, a stirring device using the cell according to Embodiment 4 of the present invention is described. FIG. 4 is a perspective view showing the structure of a stirring device according to this embodiment.

A stirring device 40 according to this embodiment is the same as the stirring device of Embodiment 2, except that it has a light entrance for allowing light to enter a container 41 and a light exit for allowing the light to exit from the container 41.

A liquid sample retaining section 43 of the container 41 contains reagent-coated particles 42, and a liquid sample supply inlet is composed of an opening 44 of the container 41 and a pipe 45 penetrating the wall of the container 41 through the opening 44. The diameter of an opening 46 of a pipe 45 located outside the container 41 is greater than the diameter of an opening 47 of the pipe 45 located inside the container 41.

The container 41 has, in its walls, an optical measurement section 48 including an incident light window 481, which serves as the light entrance, and a transmitted light window 482, which serves as the light exit.

The incident light window 481 and the transmitted light window 482 are substantially flat and made of polystyrene which is a material that is optically transparent, and the plane of the transmitted light window 482 is disposed so as to be substantially parallel to the plane of the incident light window 481.

This embodiment can produce essentially the same action and effect as those of Embodiment 2, and in addition, it enables easy and reliable optical measurements.

A liquid sample is supplied into the container 41. After the lapse of a predetermined time therefrom, light is irradiated substantially perpendicularly to the incident light window 481 from a light source (not shown). The light enters the container 41 from the incident light window 481, passes through a liquid mixture of the liquid sample and a reagent in the container 41, and exits from the container 41 through the transmitted light window 482. This light is then received by a light receiving section (not shown). Based on the intensity of the light received by the light receiving section, the absorbance or turbidity of the liquid mixture is determined, whereby the reaction between the liquid sample and the reagent can be measured.

As described above, the stirring device 40 of this embodiment has the optical measurement section 48 including the incident light window 481 serving as the light entrance and the transmitted light window 482 serving as the light exit. Therefore, in performing an optical measurement, there is no need to transfer the liquid mixture from the container 41 into another optical cell, thereby enabling a prompt spectroscopic measurement of the reaction caused by stirring. As a result, the measurement time can be further shortened. When measuring a transitional change of reaction, in particular, the transitional change can be captured in a reliable manner with little time loss. Further, since no mechanism is necessary for transferring the liquid mixture into an optical cell, the constitution of the measuring apparatus can be simplified.

Embodiment 5

Figure 5:
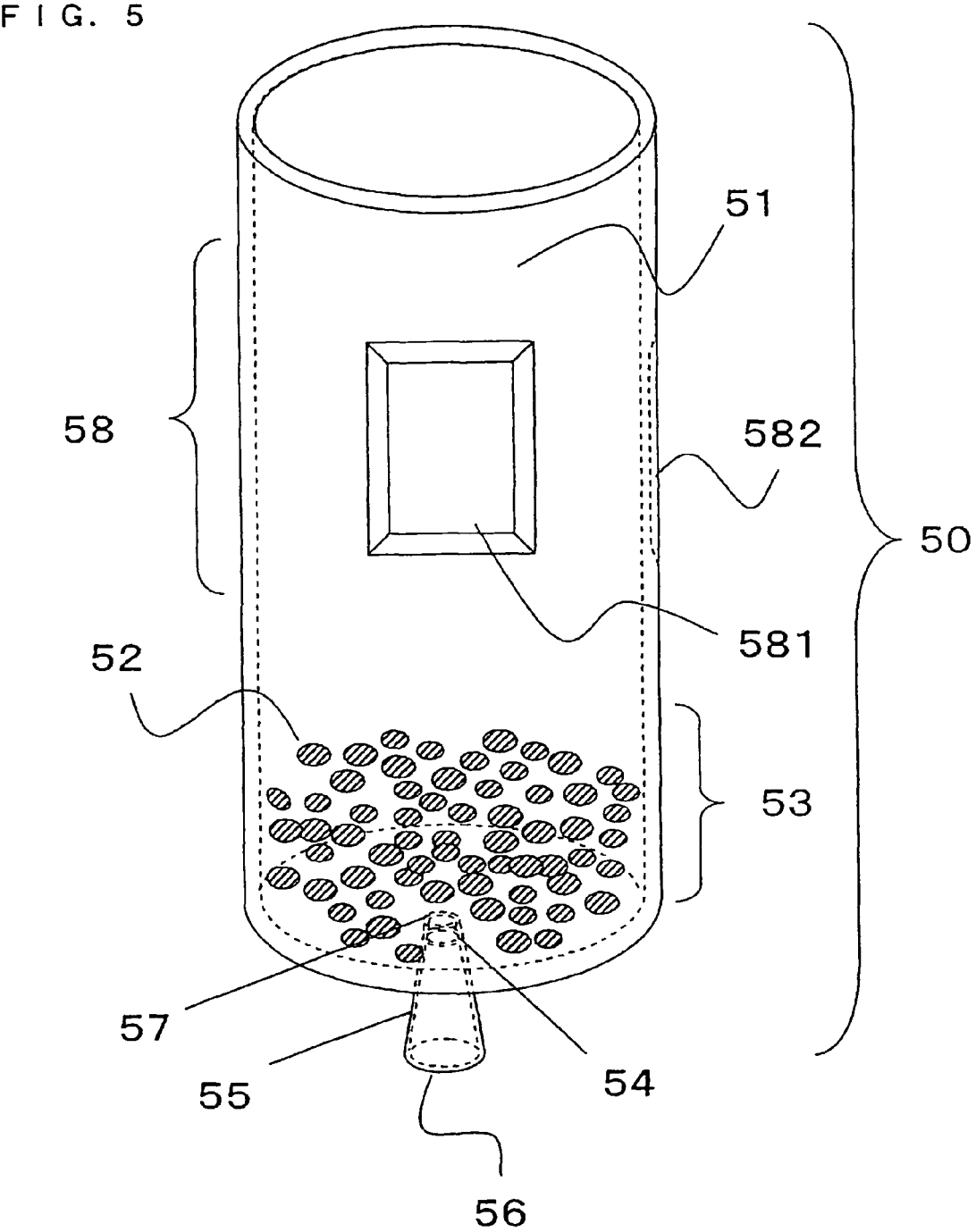
FIG. 5 is a perspective view showing the structure of a stirring device according to Embodiment 5 of the present invention.

Referring now to FIG. 5, a stirring device using the cell according to Embodiment 5 of the present invention is described. FIG. 5 is a perspective view showing the structure of a stirring device according to this embodiment.

A stirring device 50 according to this embodiment is the same as the stirring device of Embodiment 1, except that it has a light entrance for allowing light to enter a container 51 and a light exit for allowing the light to exit from the container 51.

A liquid sample retaining section 53 of the container 51 contains reagent-coated particles 52, and a liquid sample supply inlet is composed of an opening 54 of the container 51 and a pipe 55 penetrating the wall of the container 51 through the opening 54. The diameter of an opening 56 of a pipe 55 located outside the container 51 is greater than the diameter of an opening 57 of the pipe 55 located inside the container 51.

The container 51 has, in its walls, an optical measurement section 58 including an incident light window 581, which serves as the light entrance, and a scattered light window 582, which serves as the light exit.

The incident light window 581 and the scattered light window 582 are substantially flat and made of polystylene which is a material that is optically transparent, and the plane of the scattered light window 582 is disposed so as to be substantially perpendicular to the plane of the incident light window 581.

This embodiment can produce essentially the same action and effect as those of Embodiment 1, and in addition, it enables easy and reliable optical measurements.

A liquid sample is supplied into the container 51. After the lapse of a predetermined time therefrom, light is irradiated substantially perpendicularly to the incident light window 581 from a light source (not shown). The light enters the container 51 from the incident light window 581 and scatters in a liquid mixture of the liquid sample and a reagent in the container 51. The scattered light exits from the container 51 through the scattered light window 582. Or, fluorescence resulting from the incident light in the liquid mixture exits from the container 51 through the scattered light window 582.

The light or fluorescence having exited therefrom is then received by a light receiving section (not shown). Based on the intensity of the light received by the light receiving section, the degree of scattering or fluorescence intensity of the liquid mixture is determined, whereby the reaction between the liquid sample and the reagent can be measured.

As described above, the stirring device 50 of this embodiment has the optical measurement section 58 including the incident light window 581 serving as the light entrance and the scattered light window 582 serving as the light exit. Therefore, in performing an optical measurement, there is no need to transfer the liquid mixture from the container 51 into another optical cell, thereby enabling a prompt spectroscopic measurement of the reaction caused by stirring. As a result, the measurement time can be further shortened. When measuring a transitional change of reaction, in particular, the transitional change can be captured in a reliable manner with little time loss. Further, since no mechanism is necessary for transferring the liquid mixture into an optical cell, the constitution of the measuring apparatus can be simplified.

Embodiment 6

Figure 6:
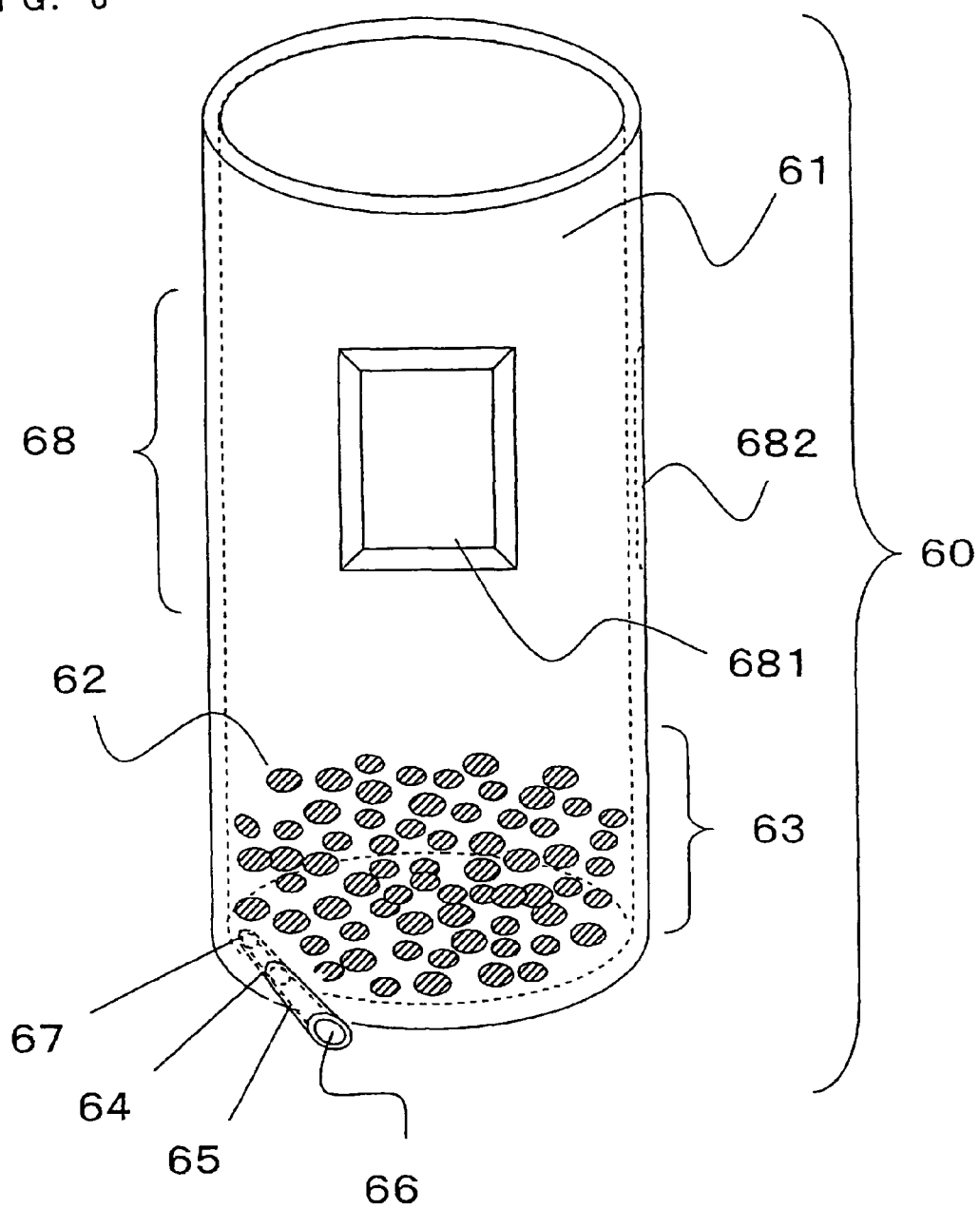
FIG. 6 is a perspective view showing the structure of a stirring device according to Embodiment 6 of the present invention.

Referring now to FIG. 6, a stirring device using the cell according to Embodiment 6 of the present invention is described. FIG. 6 is a perspective view showing the structure of a stirring device according to this embodiment.

A stirring device 60 according to this embodiment is the same as the stirring device of Embodiment 2, except that it has a light entrance for allowing light to enter a container 61 and a light exit for allowing the light to exit from the container 61.

A liquid sample retaining section 63 of the container 61 contains reagent-coated particles 62, and a liquid sample supply inlet is composed of an opening 64 of the container 61 and a pipe 65 penetrating the wall of the container 61 through the opening 64. The diameter of an opening 66 of a pipe 65 located outside the container 61 is greater than the diameter of an opening 67 of the pipe 65 located inside the container 61.

The container 61 has, in its walls, an optical measurement section 68 including an incident light window 681, which serves as the light entrance, and a scattered light window 682, which serves as the light exit.

The incident light window 681 and the scattered light window 682 are substantially flat and made of polystylene which is a material that is optically transparent, and the plane of the scattered light window 682 is disposed so as to be substantially perpendicular to the plane of the incident light window 681.

This embodiment can produce essentially the same action and effect as those of Embodiment 2, and in addition, it enables easy and reliable optical measurements.

A liquid sample is supplied into the container 61. After the lapse of a predetermined time therefrom, light is irradiated substantially perpendicularly to the incident light window 681 from a light source (not shown). The light enters the container 61 from the incident light window 681 and scatters in a liquid mixture of the liquid sample and a reagent in the container 61. The scattered light exits from the container 61 through the scattered light window 682. Or, fluorescence resulting from the incident light in the liquid mixture exits from the container 61 through the scattered light window 682.

The light or fluorescence having exited therefrom is then received by a light receiving section (not shown). Based on the intensity of the light received by the light receiving section, the degree of scattering or fluorescence intensity of the liquid mixture is determined, whereby the reaction between the liquid sample and the reagent can be measured.

As described above, the stirring device 60 of this embodiment has the optical measurement section 68 including the incident light window 681 serving as the light entrance and the scattered light window 682 serving as the light exit. Therefore, in performing an optical measurement, there is no need to transfer the liquid mixture from the container 61 into another optical cell, thereby enabling a prompt spectroscopic measurement of the reaction caused by stirring. As a result, the measurement time can be further shortened. When measuring a transitional change of reaction, in particular, the transitional change can be captured in a reliable manner with little time loss. Further, since no mechanism is necessary for transferring the liquid mixture into an optical cell, the constitution of the measuring apparatus can be simplified.

Embodiment 7

Figure 7:
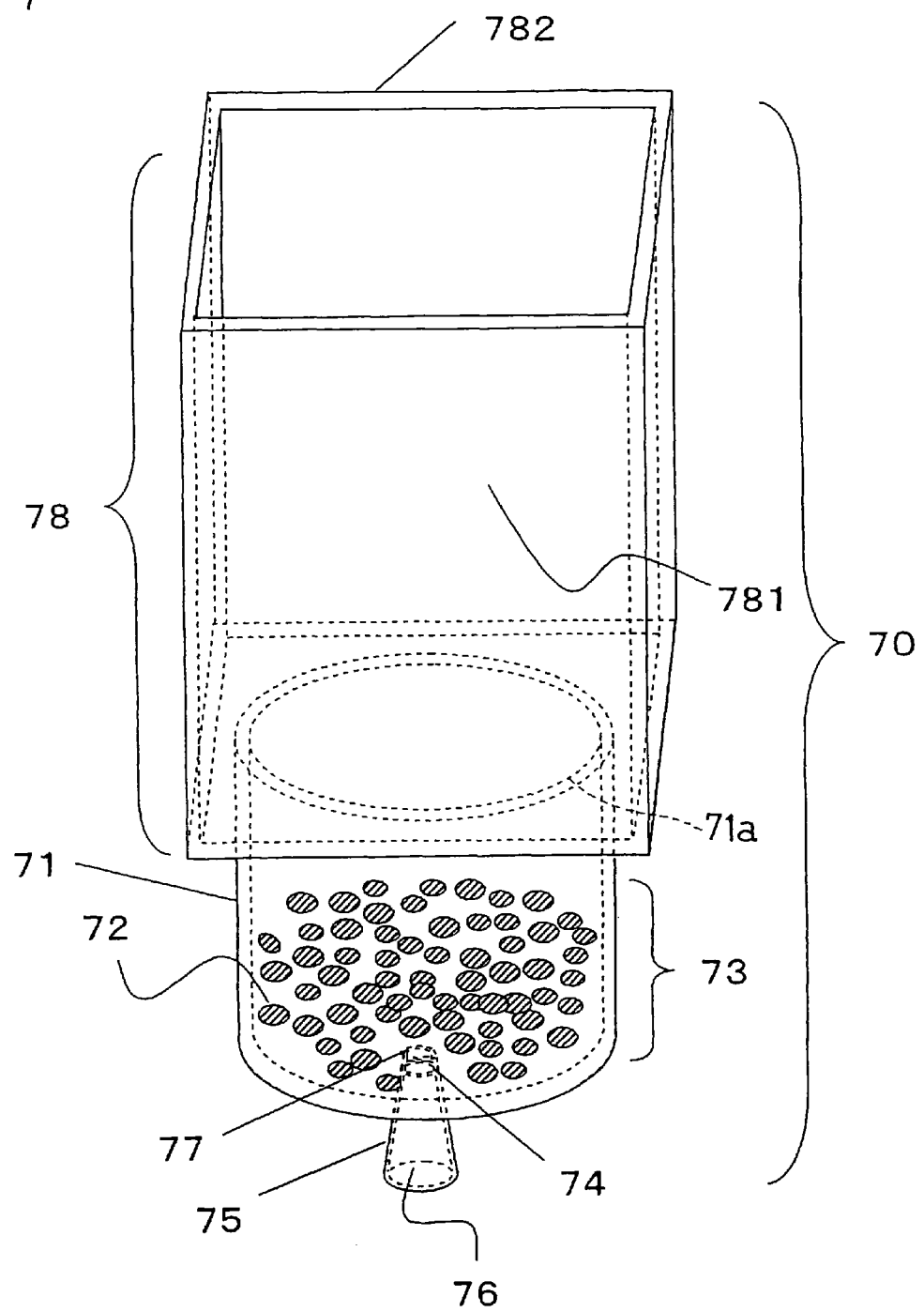
FIG. 7 is a perspective view showing the structure of a stirring device according to Embodiment 7 of the present invention.

Referring now to FIG. 7, a stirring device using the cell according to Embodiment 7 of the present invention is described. FIG. 7 is a perspective view showing the structure of a stirring device according to this embodiment.

A stirring device 70 of this embodiment is the same as the stirring device of Embodiment 3, except that the structure of the optical measurement section is changed.

A liquid sample retaining section 73 of a container 71 contains reagent-coated particles 72, and a liquid sample supply inlet is composed of an opening 74 of the container 71 and a pipe 75 penetrating the wall of the container 71 through the opening 74. The diameter of an opening 76 of a pipe 75 located outside the container 71 is greater than the diameter of an opening 77 of the pipe 75 located inside the container 71.

In Embodiment 3, the container 31 has the optical measurement section 38, but in this embodiment an optical measurement section 78 is a cylinder with a bottom, joined to an upper opening 71*a* of the container 71. The bottom of the optical measurement section 78 has an opening communicating with the upper opening 71*a* such that liquid can move between the optical measurement section 78 and the container 71.

The optical measurement section 78 is substantially flat and made of polystylene which is optically transparent. Of the planes constituting the optical measurement section 78, two opposite planes function as an optical measurement window 781 serving as a light entrance and an optical measurement window 782 serving as a light exit.

This embodiment can produce essentially the same action and effect as those of Embodiment 3, and in addition, it enables simply structured apparatus because no special process or grinding is needed to make a part of the wall of the container transparent due to the shape of the optical measurement section in this embodiment. For example, a through hole is formed on the lower portion of a commercially available and a container having an opening for introducing a liquid sample or a reagent and a liquid sample retaining section. Also, by the above manner, a cell applicable to a cell holder of a commercially available spectroscopical apparatus device can be formed and thus a useful cell capable of optical measurement can be provided.

It is noted that the case in which, of the planes constituting the optical measurement section, two opposite planes function as an optical measurement window serving as a light entrance and an optical measurement window serving as a light exit. The present invention is not limited to this embodiment. For example, of the planes constituting the optical measurement section, two planes perpendicular to each other may function as an optical measurement window serving as a light entrance and an optical measurement window serving as a light exit. The number of the optical measurement window is not limited to two and may be three or more.

Embodiment 8

Figure 8:
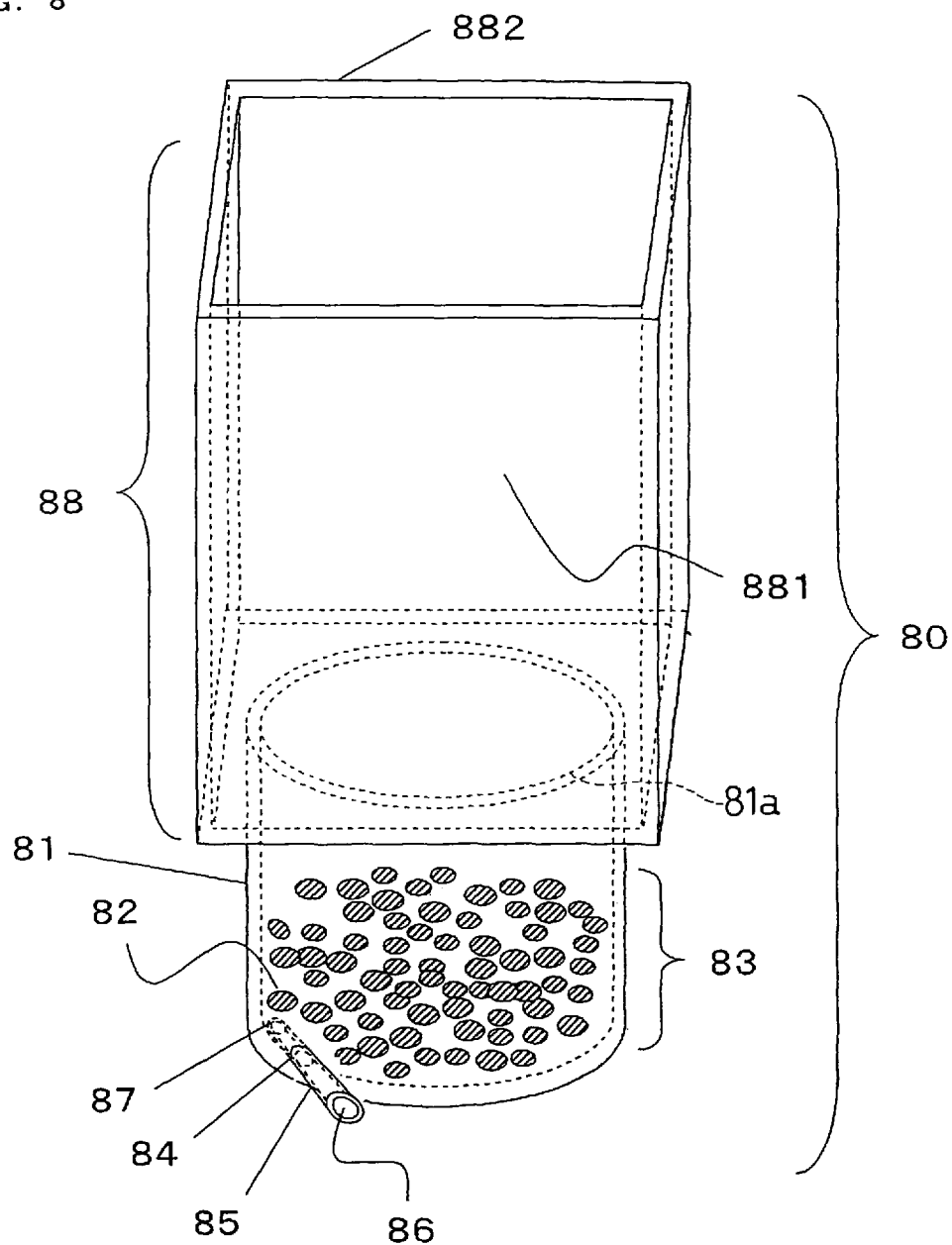
FIG. 8 is a perspective view showing the structure of a stirring device according to Embodiment 8 of the present invention.

Referring now to FIG. 8, a stirring device using the cell according to Embodiment 8 of the present invention is described. FIG. 8 is a perspective view showing the structure of a stirring device according to this embodiment.

A stirring device 80 of this embodiment is the same as the stirring device of Embodiment 4, except that the structure of the optical measurement section is changed.

A liquid sample retaining section 83 of a container 81 contains reagent-coated particles 82, and a liquid sample supply inlet is composed of an opening 84 of the container 81 and a pipe 85 penetrating the wall of the container 81 through the opening 84. The diameter of an opening 86 of a pipe 85 located outside the container 81 is greater than the diameter of an opening 87 of the pipe 85 located inside the container 81.

In Embodiment 4, the container 41 has the optical measurement section 48, but in this embodiment an optical measurement section 88 is a cylinder with a bottom, joined to an upper opening 81*a* of the container 81. The bottom of the optical measurement section 88 has an opening communicating with the upper opening 81*a* such that liquid can move between the optical measurement section 88 and the container 81.

The optical measurement section 88 is substantially flat and made of polystylene which is optically transparent. Of the planes constituting the optical measurement section 88, two opposite planes function as an optical measurement window 881 serving as a light entrance and an optical measurement window 882 serving as a light exit.

This embodiment can produce essentially the same action and effect as those of Embodiment 4, and in addition, it enables simply structured apparatus because no special process or grinding is needed to make a part of the wall of the container transparent due to the shape of the optical measurement section in this embodiment. For example, a through hole is formed on the lower portion of a commercially available and a container having an opening for introducing a liquid sample or a reagent and a liquid sample retaining section. Also, by the above manner, a cell applicable to a cell holder of a commercially available spectroscopical apparatus device can be formed and thus a useful cell capable of optical measurement can be provided.

It is noted that the case in which, of the planes constituting the optical measurement section, two opposite planes function as an optical measurement window serving as a light entrance and an optical measurement window serving as a light exit. The present invention is not limited to this embodiment. For example, of the planes constituting the optical measurement section, two planes perpendicular to each other may function as an optical measurement window serving as a light entrance and an optical measurement window serving as a light exit. The number of the optical measurement window is not limited to two and may be three or more.

Embodiment 9

Figure 9:
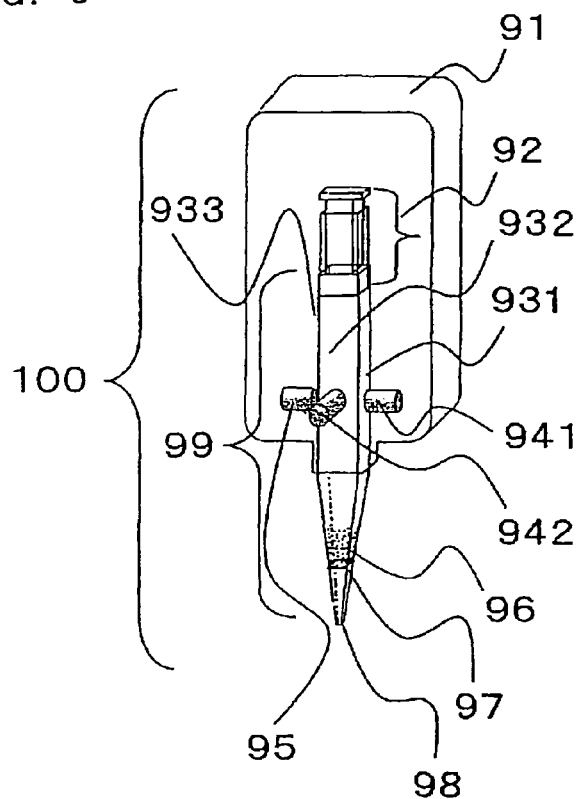
FIG. 9 is a perspective view showing the structure of a stirring device according to Embodiment 9 of the present invention.
Figure 10:
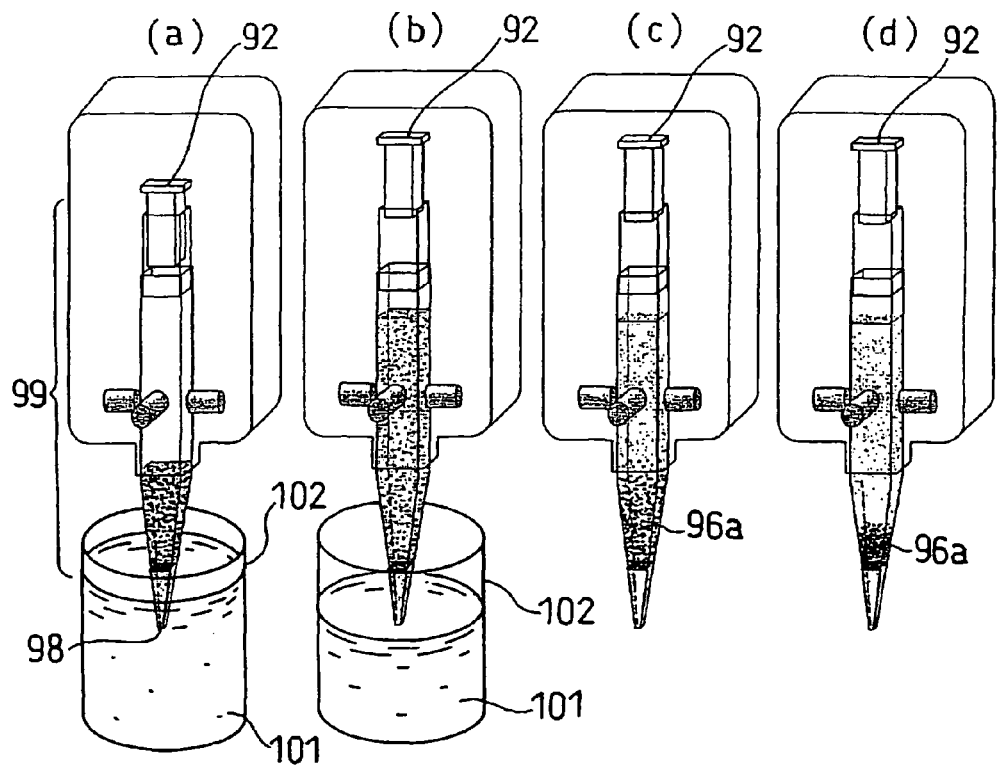
FIG. 10 are diagrams which describe the operations of the stirring device according to Embodiment 9 of the present invention.

Referring now to FIGS. 9 and 10, a stirring device (analyzer) using the cell according to Embodiment 9 of the present invention is described. FIG. 9 is a schematic perspective view showing the structure of an analyzer according to this embodiment. Also, FIG. 10 shows the operations of the analyzer 100 of FIG. 9.

The analyzer 100 of this embodiment includes a housing 91 and a stirring device 99 (corresponding to the cell of the present invention) formed of a cylinder having a plunger 92. The stirring device 99 is accommodated in the housing 91. The cylinder has a rectangular cross section, and its side faces function as an incident light window 933, a transmitted light window 931 and a scattered light window 932. The lower part of the cylinder tapers down, and the opening of the tip functions as a liquid sample supply inlet 98.

In the housing 91, the stirring device 99 has, on its side faces, a light source 95, a transmitted light detector 941 and a scattered light detector 942. As the transmitted light detector 941 and the scattered light detector 942, photodiodes for visible light detection are used.

Also, the transmitted light window 931, the scattered light window 932 and the incident light window 933 are disposed such that the plane of the transmitted light window 931 is parallel to the plane of the incident light window 933 and that the plane of the scattered light window 932 is perpendicular to the plane of the incident light window 933.

Inside the stirring device 99, reagent-coated particles 96 coated with an immunoassay reagent including an immunoreactive substance, which causes an antigen-antibody reaction with an analyte in a liquid sample, are provided.

The incident light window 933, the transmitted light window 931 and the scattered light window 932 are substantially flat and made of polystyrene which is optically transparent. Also, the light source 95 is disposed so as to be perpendicular to the plane of the incident light window 933, while the detection plane of the transmitted light detector 941 and the detection plane of the scattered light detector 942 are disposed so as to be perpendicular to the transmitted light window 931 and the scattered light window 932, respectively.

The other parts of the stirring device 99 are made of polypropylene. Also, as the reagent-coated particles 96, the same particles as those of Embodiment 1 are used.

Referring now to FIG. 10, the operations of the analyzer 100 of this embodiment are described. As illustrated in FIG. 10(a), first, the liquid sample supply inlet 98 is submerged into a liquid sample 101 in a beaker 102, and a plunger 92 is pulled upward. Then, the liquid sample 101 flows in from the liquid sample supply inlet 98, and this flow moves the reagent-coated particles 96 upward from the mesh 97. As a result, the reagent-coated particles 96 are suspended in the liquid sample 101 in the stirring device 99, and due to the movement of the reagent-coated particles 96, the reagent coated on the surfaces of the reagent-coated particles 96 is dissolved in the liquid sample 101.

Subsequently, when the plunger 92 is pulled up to the position as shown in FIG. 10(b) and held there, the reagent-coated particles 96 float up to the level of the incident light window 933, the transmitted light window 931, and the scattered light window 932.

However, after the dissolution of the reagent from the reagent-coated particles 96, the particles have a large specific gravity, so they gradually settle down below the level of the incident light window 933, the transmitted light window 931, and the scattered light window 932, as illustrated in FIGS. 10(c) and (d). Accordingly, the turbidity caused by the antigen-antibody reaction between the analyte in the liquid sample 101 and the reagent can be measured optically.

After the particles have settled down, light is irradiated substantially perpendicularly to the incident light window 933 from the light source 95. The incident light from the incident light window 933 passes through a liquid mixture of the liquid sample and the reagent. At this time, light traveling substantially straight then passes through the transmitted light window 931 and is received by the transmitted light detector 941. Also, the light scattered by the reaction products in the liquid mixture passes through the scattered light window 932 and is received by the scattered light detector 942.

Based on the intensity of the light received by the transmitted light detector 941 and the scattered light detector 942, the reaction between the liquid sample and the reagent can be measured.

The absorbance or turbidity detected by the transmitted light detector 941, and the scattered light intensity detected by the scattered light detector 942 can be used as indexes of the reaction between a liquid sample and a reagent. Any of these indexes may be used to measure the reaction between a liquid sample and a reagent; however, if the turbidity caused by the reaction is low, the use of scattered light intensity enables measurements with higher sensitivity.

In this embodiment, the stirring device 99 may be replaced with another stirring device. For example, a stirring device 110 with the structure of FIG. 11 may also be used.

Figure 11:
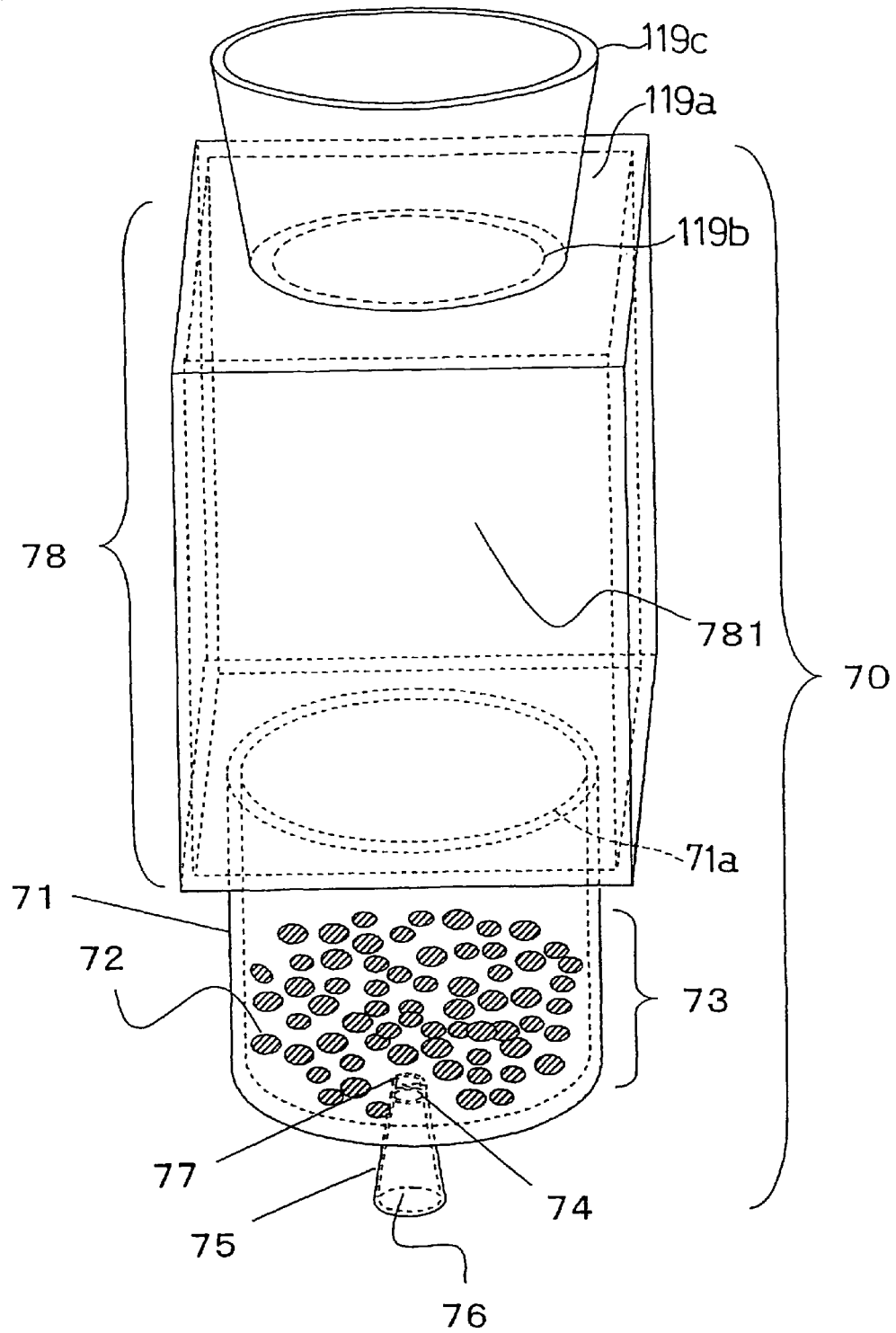
FIG. 11 is a perspective view of a modified example of the stirring device according to Embodiment 9 of the present invention.

The stirring device 110 of FIG. 11 is structured such that the stirring device of FIG. 7 according to Embodiment 7 of the present invention is fitted with a cover 119a having an opening 119b and that the opening 119b is fitted with a funnel-shaped guide 119c. The guide 119c is to receive the plunger 92.

Likewise, stirring devices as illustrated in FIGS. 3 to 8 which are further provided with a cover, an opening and a funnel-shaped guide may also be used.

As described above, by fitting the stirring device 99 with the plunger 92, the analyzer 100 of this embodiment can mix and stir a liquid sample and a reagent in a prompt and easy manner, simultaneously with the sampling of the liquid sample.

In this embodiment, the stirring device 99 is provided with the incident light window 933, the transmitted light window 931 and the scattered light window 932. Also, the light source 95 is disposed so as to be perpendicular to the incident light window 933, while the detection plane of the transmitted light detector 941 and the detection plane of the scattered light detector 942 are disposed so as to be perpendicular to the transmitted light window 931 and the scattered light window 932, respectively.

Therefore, using a liquid mixture obtained by mixing and stirring a liquid sample and a reagent, an antigen-antibody reaction can be promptly measured spectroscopically, and the measurement time can be further shortened. When measuring a transitional change of reaction, in particular, the transitional change can be captured in a reliable manner with little time loss. Further, since no mechanism is necessary for transferring the liquid mixture into an optical cell, the constitution of the measuring apparatus can be simplified.

INDUSTRIAL APPLICABILITY

The stirring method, cell and stirring device of the present invention can stir a liquid sample and a reagent in a prompt and easy manner with a simple structure. Accordingly, the present invention is useful, for example, for test devices (particularly POCT devices), such as immunochemical analyzers and biochemical analyzers, used, for example, in clinical tests that make chemical analyses of liquid samples, such as blood and urine.

The invention claimed is:

1. A method for stirring a liquid sample containing an analyte and a reagent, said method comprising the steps of:
   (A) providing a cell comprising: a liquid sample retaining section having a plurality of particles with a surface covered with said reagent, and a liquid sample supply inlet, and supplying a liquid sample containing an analyte from said liquid sample supply inlet to said liquid sample retaining section; and
   (B) stirring said liquid sample and said reagent by the movement of said particles caused by the flow of said liquid sample in said liquid sample retaining section resulting from the supply of said liquid sample, to separate said reagent from the surface of the particles and to obtain a liquid mixture containing said liquid sample, said reagent, which is dissolved in the liquid sample and said particles,
   wherein said reagent includes a specific binding substance capable of specifically binding with an analyte in said liquid sample, and
   an electric charge of the surface of said particles and an electric charge of said specific binding substance have a positive polarity in said liquid mixture,
   wherein, the method further comprises the following step between step (A) and step (B):
   a step of adjusting pH in said liquid mixture to be a pH of less than the isoelectric point pI of the reagent.

2. The stirring method in accordance with claim 1, wherein the flow of said liquid sample in said step (B) is a flow circulating along the inner face of the wall of said liquid sample retaining section.

3. The stirring method in accordance with claim 1, wherein said reagent is an antibody.

4. The stirring method in accordance with claim 1, wherein each surface of said plurality of particles comprises amino groups.

5. The stirring method in accordance with claim 3, wherein each surface of said plurality of particles comprises amino groups.

6. The stirring method in accordance with claim 4, wherein each surface of said plurality of particles comprises polysine.

7. The stirring method in accordance with claim 5, wherein each surface of said plurality of particles comprises polylysine.

8. A method for stirring a liquid sample containing an analyte and a reagent, said method comprising the steps of:
   (A) providing a cell comprising: a liquid sample retaining section having a plurality of particles with a surface covered with said reagent, and a liquid sample supply inlet, and supplying a liquid sample containing an analyte from said liquid sample supply inlet to said liquid sample retaining section; and
   (B) stirring said liquid sample and said reagent by the movement of said particles caused by the flow of said liquid sample in said liquid sample retaining section resulting from the supply of said liquid sample, to separate said reagent from the surface of the particles and to obtain a liquid mixture containing said liquid sample, said reagent, which is dissolved in the liquid sample and said particles,
   wherein said reagent includes a specific binding substance capable of specifically binding with an analyte in said liquid sample,
   an electric charge of the surface of said particles and an electric charge of said specific binding substance have a negative polarity in said liquid mixture,
   the method further comprises the following step between step (A) and step (B):
   a step of adjusting pH in said liquid mixture to be a pH of more than the isoelectric point pI of the reagent.

9. The stirring method in accordance with claim 7, wherein the flow of said liquid sample in said step (B) is a flow circulating along the inner face of the wall of said liquid sample retaining section.

10. The stirring method in accordance with claim 8, wherein said reagent is antibody.

11. The stirring method in accordance with claim 8, wherein each surface of said plurality of particles comprises sulfonic acid groups or carboxyl groups.

12. The stirring method in accordance with claim 10, wherein each surface of said plurality of particles comprises sulfonic acid groups or carboxyl groups.

* * * * *

UNITED STATES PATENT AND TRADEMARK OFFICE
CERTIFICATE OF CORRECTION

PATENT NO.         : 7,790,470 B2                                                                Page 1 of 1
APPLICATION NO.    : 10/588546
DATED              : September 7, 2010
INVENTOR(S)        : Akihito Kamei et al.

It is certified that error appears in the above-identified patent and that said Letters Patent is hereby corrected as shown below:

In the Claims, in Column 20, Line 30 (Claim 9), The stirring method in accordance with claim 7..., should read, The stirring method in accordance with claim 8....

Signed and Sealed this

Twenty-third Day of November, 2010

David J. Kappos
*Director of the United States Patent and Trademark Office*